United States Patent
Phan et al.

(10) Patent No.: US 6,559,457 B1
(45) Date of Patent: May 6, 2003

(54) SYSTEM AND METHOD FOR FACILITATING DETECTION OF DEFECTS ON A WAFER

(75) Inventors: Khoi A. Phan, San Jose, CA (US); Bharath Rangarajan, Santa Clara, CA (US); Bhanwar Singh, Morgan Hill, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/534,410

(22) Filed: Mar. 23, 2000

(51) Int. Cl.[7] ................... H01J 37/20; H01J 37/304; G03F 9/00

(52) U.S. Cl. ................ 250/491.1; 250/492.2; 250/398; 250/310

(58) Field of Search .............. 250/310, 491.1, 250/492.2, 398

(56) References Cited

U.S. PATENT DOCUMENTS

| | | | | |
|---|---|---|---|---|
| 4,442,361 A | * | 4/1984 | Zasio et al. | 250/491.1 |
| 5,847,821 A | | 12/1998 | Tracy et al. | 356/237 |
| 6,122,562 A | * | 9/2000 | Kinney et al. | 700/121 |
| 6,324,298 B1 | * | 11/2001 | O'Dell et al. | 382/149 |

* cited by examiner

Primary Examiner—Bruce Anderson
Assistant Examiner—Nikita Wells
(74) Attorney, Agent, or Firm—Amin & Turocy, LLP

(57) ABSTRACT

The present invention relates to detecting defects on a wafer. A wafer stage includes markings which are used to form a reference coordinate system. The wafer is positioned on the wafer stage and the wafer is scanned to detect a defect on the wafer. The position of the detected defect is mapped relative to the reference coordinate system of the stage. The location of a reference point on the wafer also is determined in the reference coordinate system. The position of the defect is determined relative to the reference point on the wafer so as to facilitate repeatedly locating the defect on the wafer as the wafer is loaded and reloaded into inspection and processing tools.

20 Claims, 5 Drawing Sheets

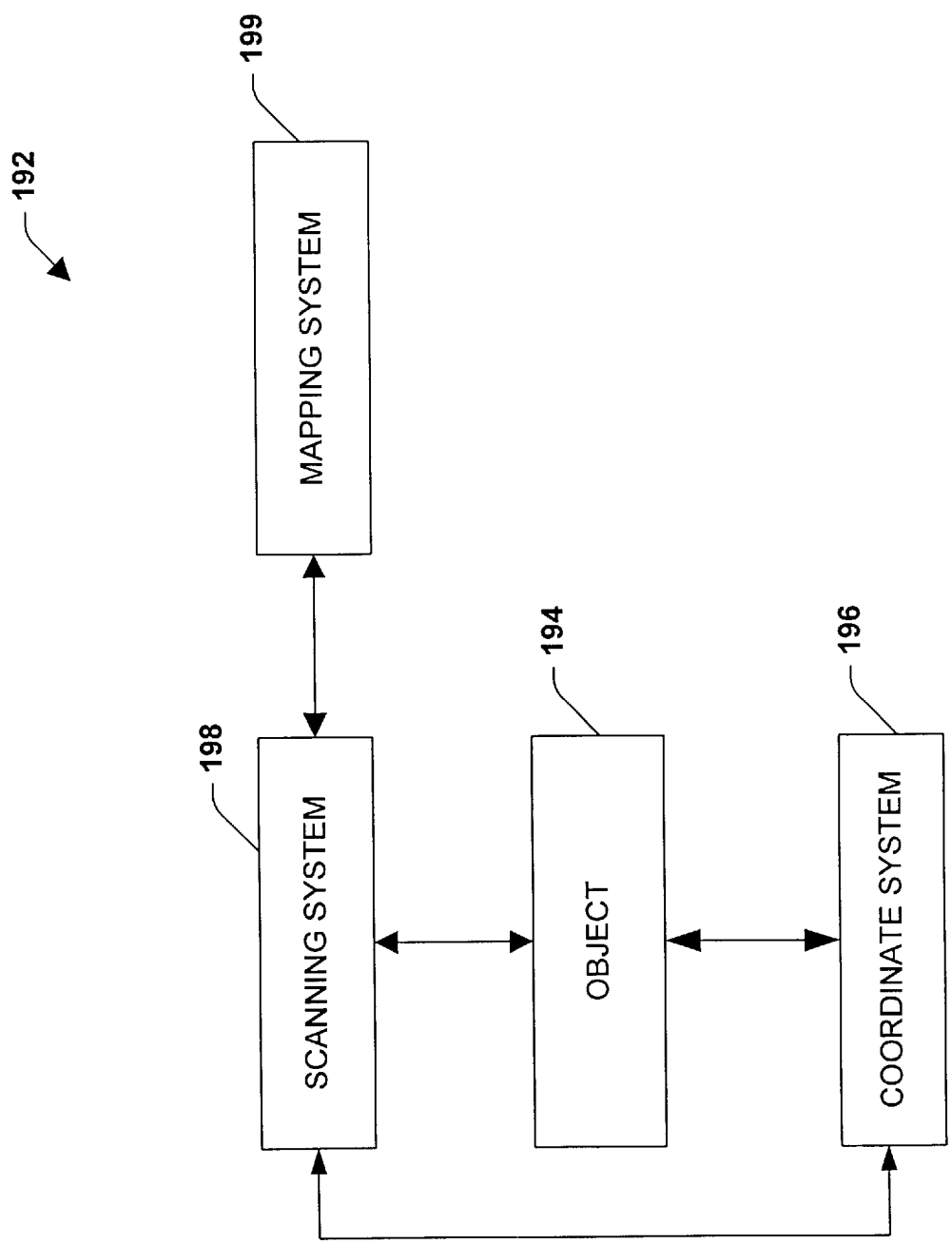

SYSTEM AND METHOD FOR FACILITATING DETECTION OF DEFECTS ON A WAFER

TECHNICAL FIELD

The present invention generally relates to semiconductor processing and, more particularly, to a system and method for facilitating detection of defects on a wafer.

BACKGROUND OF THE INVENTION

The tendency of semiconductor devices such as integrated circuits (IC) and large scale integrated circuits (LSIC) toward minuteness has rapidly progressed, and higher accuracy has been required of apparatuses for manufacturing such semiconductor devices. In particular, such requirements are demanded from exposure devices in which a circuit pattern of a mask or a reticle is superposedly transferred onto a circuit pattern formed on a semiconductor wafer. It is desired that the circuit pattern of the mask and the circuit pattern of the wafer be superposed one upon the other with accuracies of, for example, less than 0.1 $\mu$m.

In order to remain competitive, semiconductor manufacturers continually strive to reduce costs associated with manufacturing semiconductor chips while at the same time improving yield in the manufacturing process. However, wafer defects typically result in decreased yield and, in turn, provide associated increases in the manufacturing cost. Some defects exist, for example, on blank wafers as purchased. Other defects might be caused during manufacturing, such as by one of the process tools into which the wafer is placed.

Various methodologies exist for detecting and analyzing defects on wafer surfaces. One type of detector is a laser surface particle detector (LSPD) which measures amount, location, and size of particles on the wafer surface. A scanning electron microscope (SEM) equipped with an energy dispersive x-ray spectroscopy (EDS) system often is used to generate chemical information about the wafer surface layer. Because the LSPD by itself may not be sufficient for identifying a source of the particles, the LSPD system may be combined with the SEM/EDS system to locate particles on the wafer surface and to analyze the particles, respectively. The combined system is known as a particle analysis system (PAS), which is commonly used throughout the semiconductor industry. A coordinate system employed by the SEM usually is not the same as that used by the LSPD. Consequently, appropriate coordinate transforms are utilized to convert position data between the two coordinate systems.

In order to improve yield and reduce manufacturing costs, it is desirable to minimize defects caused by processing tools. Accordingly, various inspection tools, such as those commercially available from KLA-Tencor and Inspex, have been developed to map and record wafer surface defects. One particular approach to obtain information about individual specific processing tools is to employ blank test wafers during test procedures. For example, it is known to utilize a blank wafer that is marked with at least two fiducial marks. The number and position of any initial defects on the blank wafer are determined relative to the fiducial marks and the relative coordinates of the initial defects and fiducial marks are recorded. The wafer is then placed in a selected process tool and processed accordingly. The processed wafer is then analyzed again, such as in a LSPD, to determine the number and position of additional defects caused by the process tool and the coordinates of each additional defect is recorded. An analysis tool may then be employed to analyze each of the additional defects by mapping the coordinates of the defects and fiducial marks from the LSPD to the coordinate frame of the analysis tool using an appropriate coordinate transform. However, the fiducial marks occupy valuable wafer real estate, which is an ever increasingly desired commodity in light of market demands for increased device density.

There is a strong need in the art for a system and/or methodology which mitigates at least some of the short comings of convention defect detection systems and/or methods.

SUMMARY OF THE INVENTION

The present invention relates to a system and method for facilitating detection of wafer defects.

A wafer is supported by the surface of a stage, support or platform (hereinafter referred to by "stage"). The surface of the stage has a coordinate system associated therewith, and preferably surface markings coincident with the coordinate system. Preferably, the wafer has at least one edge mark to facilitate determining wafer orientation via the stage coordinate system. The stage markings are employed to facilitate determining position of a wafer placed on the stage, and to facilitate mapping to points of interest (e.g., defect locations) on the wafer. For example, when a wafer is placed on the stage, the stage markings are employed to facilitate determining the size of the wafer, the position of the wafer relative to the stage and the location of various sections of the wafer relative to the stage. A wafer surface defect procedure may be employed on the wafer, and the location of wafer surface defects determined and those locations stored in a memory. If the wafer is removed from the stage and later placed back on the stage, the present invention can readily determine the location of the defects by the mappings stored in the memory. The wafer does not have to be placed in the same location and/or orientation as it was earlier placed. The stage coordinate system provides for determining the location and/or orientation of the wafer, and for relocating wafer surface defects based on the earlier mappings thereof.

The present invention mitigates the need for employing fiducial marks on the surface of the wafer as compared to conventional systems. As a result, the present invention facilitates efficient utilization of valuable wafer surface real estate.

One aspect of the present invention relates to a system for facilitating detection of defects on a wafer. A stage receives the wafer, and the stage has a plurality of reference markings which form a reference coordinate system. A scanning system associated with the stage locates defect(s) of the wafer. The defects are mapped relative to the reference coordinate system of the stage.

Another aspect of the present invention relates to a system for facilitating detection of defects on a wafer. The system includes reference means for receiving the wafer and providing a reference coordinate system; and means for mapping a defect of the wafer relative to the reference coordinate system.

Another aspect of the present invention relates to a method for facilitating detection of defects on a wafer located on a stage. Reference markings on the stage are located, and defects of the wafer relative to the reference markings of the stage are mapped.

Still another aspect of the present invention relates to a system for mapping a wafer. A support system supports the wafer—the support system has a reference system associated therewith. A locating system determines via the reference system a position and orientation of the wafer relative to the support system. A mapping system maps the position and orientation of the wafer based on information from the locating system. The mapping system also maps at least one point of interest on the wafer surface. A storing system stores the mapping information.

Another aspect of the present invention relates to a system for mapping a wafer. A stage supports the wafer—the stage includes a plurality of reference marks. A first system determines location and orientation of the wafer relative to the stage via the reference marks. A second system detects points of interest on the wafer. A third system determines the location of the points of interest relative to the wafer via the reference marks. A fourth system maps the location of the points of interest relative to the wafer. It is to be appreciated that this aspect of the present invention is not limited to four sub-systems, and that any number (N) of sub-systems may be employed to carry out one or all of the functions of the aforementioned four sub-systems.

Yet another aspect of the present invention relates to a wafer stage. The stage includes a top surface for supporting a wafer—the top surface includes a plurality of reference marks which facilitate determining a location and orientation of the wafer relative to the stage. The reference marks also facilitate determining a location of at least one point of interest on the wafer relative to the wafer and stage.

To the accomplishment of the foregoing and related ends, the invention, then, comprises the features hereinafter fully described and particularly pointed out in the claims. The following description and the annexed drawings set forth in detail certain illustrative examples of the invention. These examples are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 2a is a schematic block diagram of an apparatus for locating wafer defects in accordance with the present invention;

DETAILED DESCRIPTION OF THE INVENTION

Figure 1:
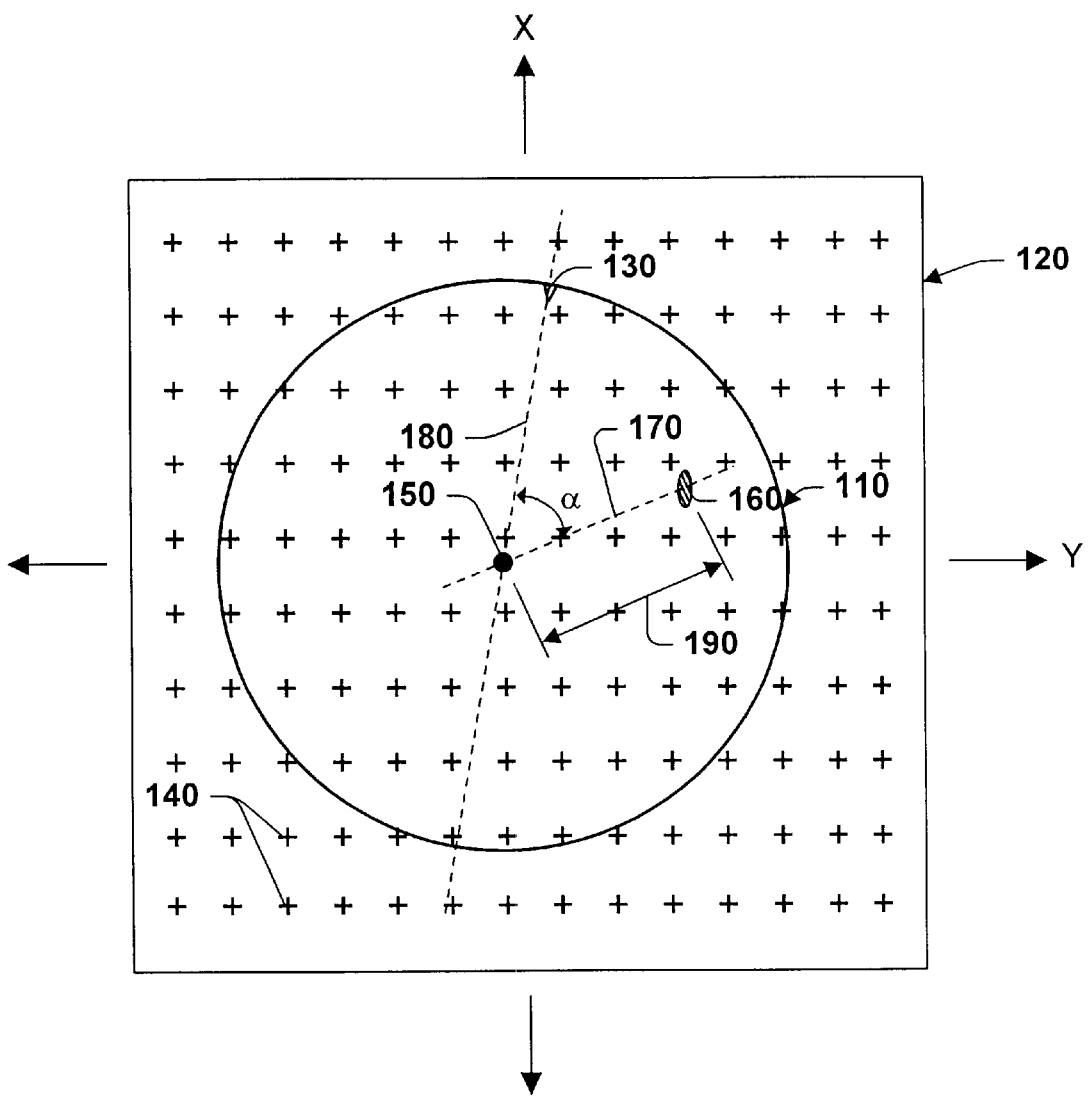
FIG. 1 is a schematic illustration of a wafer disposed on a stage for facilitating detection of a defect in accordance with the present invention.

The present invention will now be described with reference to the drawings, wherein like reference numerals are used to refer to like elements throughout.

FIG. 1 is a schematic illustration of a blank wafer 110 positioned on a wafer stage 120 in accordance with the present invention to facilitate detection of wafer defects. The wafer 110 includes an alignment orientation feature 130, such as a notch or a flat edge along its perimeter. The orientation feature 130 is used to determine relative orientation of the wafer 110 as it is loaded into various process tools. Preferably, the orientation feature 130 is a notch, however, any suitable orientation feature may be employed. The present invention mitigates the need for other wafer markings (e.g., fiducial marks), and thus facilitates maximizing availability of wafer real estate.

In accordance with the present invention, the stage 120 is provided with a plurality of reference markings 140. The reference markings 140 are illustrated as a series of "+" signs arranged in a grid-like pattern, however, any suitable mark schema may be employed and is intended to fall within the scope of the hereto appended claims. The grid-like pattern forms a reference coordinate system (e.g., a Cartesian coordinate system) having X and Y coordinate axes. It is to be understood and appreciated that, while the example of FIG. 1 illustrates a Cartesian coordinate system, other types of coordinate systems (e.g., polar) also could be used. It will be appreciated that, even if the wafer 110 visually obstructs some of the reference markings 140, the reference coordinate system of the stage 120 may be defined by extrapolating from the visible reference markings.

Once the wafer 110 is positioned on the stage 120, the position of the orientation feature 130 is located and its relative position is determined in relation to the reference coordinate system. For example, a scanning device or inspection tool is used to determine the distance of the orientation feature 130 from a pair of the reference markings 140. The X, Y-coordinates of the orientation feature 130 are easily calculated based on the detected distances from the reference markings 140. The position of the orientation feature 130 in the reference coordinate system could be determined using other positioning techniques.

The relative position of a center 150 of the wafer 110 may be calculated by employing any known semiconductor wafer center finding technique. For example, a microprocessor-based scan data processing system locates points along the circumference of the wafer 110 so as to define the wafer edge. A polar coordinate map of the wafer 110 based on the edge data is then employed to locate the center of the wafer 150. The X and Y. coordinates of the wafer center 150 are mapped into the reference coordinate system of the stage 120.

The position of the orientation feature 130 and wafer center 150 provide reference points on the wafer 110 to which other pertinent features of the wafer, including defects, may be mapped. By way of example, a scanning device, such as that employed to locate the orientation feature 130, locates a defect 160 relative to the reference coordinate system provided by the reference markings 140. The relative position of the defect 160 in the reference coordinate system is then determined relative to the wafer center 150. For purposes of explanation, a reference line 170 is drawn to extend through the wafer center 150 and the defect 160. Another reference line 180 extends through the wafer center 150 and the orientation feature 130. The line 170 between the wafer center 150 and defect 160 has a relative angle , as drawn clockwise from the notch line 180 to the other line 170. The distance between the defect 160 and wafer center 150 along the line 170 is indicated at 190. The distance 190 and relative angle , thus, provide a quantitative measurement of the position of the defect 160 relative to the wafer center 150 and orientation feature 130. As a result, the location of the defect 160 may repeatedly be determined upon locating the orientation feature 130 and wafer center 150. That is, the coordinate system printed on the stage 120 in combination with the orientation feature 130 of the wafer 110 provide a mechanism by which defects may be repeatedly located on the wafer each time the wafer is loaded and reloaded into the scanning system. In addition, the defect 160 may easily be located by other inspection instruments and tools by mapping the recorded position of the defect relative to the wafer center 150 and orientation feature 130 to that of the other instrument or tool being employed.

While, for purposes of brevity, a single defect 160 is shown and described with respect to the wafer 110 of FIG. 1, it is to be understood that there are typically a number of defects on a wafer. Such defects, regardless of number, may be located readily in accordance with the present invention. It is also to be appreciated that the size of the defect 160 relative to the wafer 110 has been exaggerated for ease of illustration. The defect 160 typically is a particle or aberration on the wafer surface.

FIG. 2a is a is a schematic block diagram of a system 192 which is employed, in accordance with the present invention, to locate and map defects of an object or article 194. The system 192 includes a reference coordinate system 194 configured to receive the object 194. For example, the object 194 is disposed onto a receiving surface of the reference coordinate system 196.

A scanning system 198 is operatively associated with the coordinate system 196 for locating the object 196 relative to the reference coordinate system. In particular, the scanning system 198 scans the surface of the object 194 to locate one or more points of interest, such as for example, a reference point of the object and one or more defects of the object. The scanning system 198 also is operatively connected with a mapping system 199 for providing information that characterizes the location of each point of interest of the object 194 in the coordinate system 196. The mapping system 199 maps the position of each defect relative to a selected one of the points of interest of the object 194 (e.g., a reference point). The mappings are stored in appropriate memory of the mapping system 199.

Based on the stored mappings, the system 192 can readily locate each defect repeatedly as the object 194 is loaded and reloaded into the coordinate system 196. The object 194 does not have to be placed in the coordinate system 196 at the same location and/or orientation as it was earlier placed. Instead, the scanning system 198 locates the reference point of the object 194 and employs the stored mappings of the defects to relocate each defect in the coordinate system 196 relative to the location of the reference point.

Figure 2B:
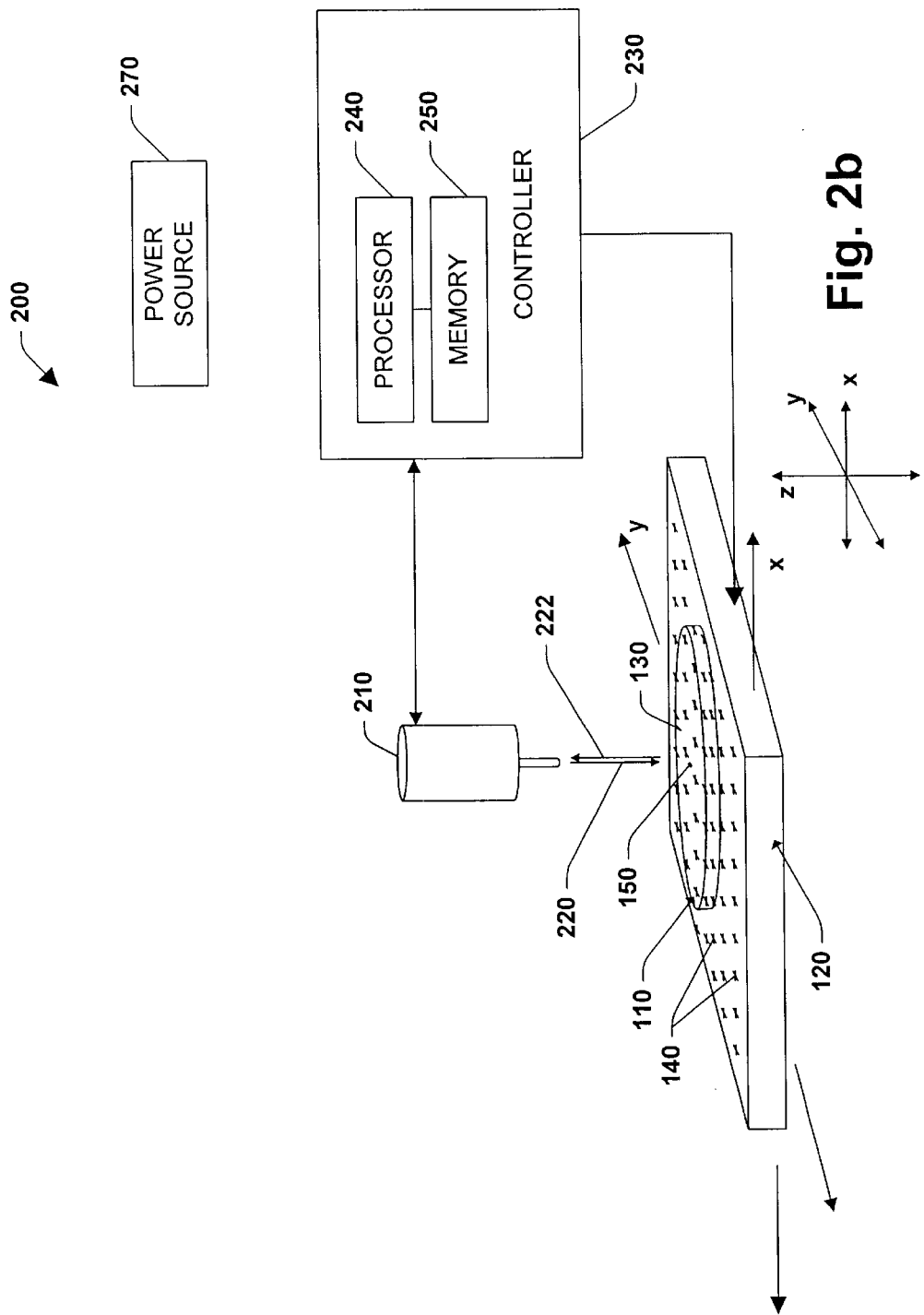
FIG. 2b is a schematic illustration of a system for locating wafer defects in accordance with the present invention.

FIG. 2b is a schematic illustration of a representative system 200 which is employed, in accordance with the present invention, to detect and map defects of the wafer 110 located on the associated stage 120. The system 200 includes a scanning system 210 that emits a signal, indicated by arrow 220, onto the surface of the wafer 110 to analyze wafer topography.

By way of example, the scanning system 210 is a scanning electron microscope (SEM) that emits a beam 220 of monochromatic electrons onto the wafer 110 (or other article being analyzed). For purposes of explanation, and not by way of limitation, the "scanning system 210" will hereinafter be referred to as the "SEM 210." The beam 220 sweeps across the wafer surface in a predetermined pattern and strikes the wafer 110 and/or the stage 120. The beam dwells on points of the wafer 110 and/or the stage 120 for a predetermined duration as set by the scan speed of the SEM 210. At each dwell point, the beam 220 interacts with the wafer 110 or stage 120, which interactions (indicated by arrow 222) are detected by associated detection instruments of the SEM 210. The detection instruments of the SEM 210 provide a signal in response to the detected interactions at each scanned area. The signal indicates position information for each scanned area, including defects, which is mapped into the reference coordinate system of the stage 120. The signal also indicates, for example, topographical and morphological information, the composition of each scanned area (including relative ratios of compounds and elements), and/or cyrstallographic information (identifying the arrangement of atoms in each scanned area). Advantageously, the SEM is operative to both locate defects on the wafer 110 and provide pertinent chemical information concerning each detected defect. The chemical information may be further processed and analyzed to better identify the source of a given defect.

While the foregoing example of the present invention has been described as employing a SEM 210 to locate and analyze defects, it is to be appreciated that the field of inspection tools is evolving rapidly and that any other type of scanning system suitable for carrying out the present invention is intended to fall within the scope of the appended claims. Examples of other types of inspection and analysis tools and techniques that may be implemented in accordance with the present invention include: a laser surface particle detector (LSPD); atomic force microscopy (AFM); a focused ion beam system (FIB); x-ray photoelectron spectroscopy (XPS); secondary ion mass spectroscopy (SIMS); field emission Auger electron spectroscopy (FEAES); and Fourier transform infrared spectroscopy (FTIR).

Referring back to FIG. 2b, the SEM 210 is connected to and controlled by a controller 230. The controller 230 includes a processor 240 that is programmed to control and operate the SEM 210 and other various components within the system 200 in order to carry out the various functions described herein. The manner in which the processor 240 can be programmed to carry out the functions relating to the present invention will be readily apparent to those having ordinary skill in the art based on the description provided herein.

A memory 250 which is operatively coupled to the processor 240 is also included in the controller 230 and serves to store program code executed by the processor 240 for carrying out operating functions of the system 200 as described herein. The memory 250 includes, for example, read only memory (ROM) and random access memory (RAM). The RAM is the main memory into which the operating system and application programs are loaded. The memory 250 also serves as a storage medium for storing information such as wafer position, coordinates of defects on the wafer, wafer coordinate tables, orientation feature information, chemical data for detected defects, programs for determining wafer center and defect locations, and other data which may be employed in carrying out the present invention. For mass data storage, the memory 250 may also include a hard disk drive (e.g., 50 Gigabyte hard drive).

A power source 270 provides operating power to the system 200. Any suitable power source (e.g., battery, line power) may be employed to implement the present invention.

The wafer stage 120 receives the wafer 110. It is to be appreciated that the wafer stage 120 may be provided for slight rotation and/or be two-dimensionally moveable in the X-direction and Y-direction. After the stage 120 is moved, the reference coordinate system should be reestablished by the SEM 210 relocating the reference markings 140. The stage 120 also may include a wafer holder (not shown) for vacuum adsorbing the wafer onto its surface. Alternatively, the stage 120 itself may be equipped with a vacuum mechanism for retaining the wafer 110. The controller 230 effects movement of the wafer stage 120 (via a plurality of motors (not shown)) for wafer alignment and positioning.

The system 200 employs the SEM 210 to find and map the locations of the orientation feature 130 and the wafer center 150. Once the locations of the orientation feature 130 and wafer center 150 (if desired) have been mapped into the reference coordinate system of the stage 120, the processor 240 can determine the location of each detected defect. The relative positions of each defect 160, the wafer center 150, and the orientation feature are recorded in the memory 250. As mentioned above, pertinent chemical data concerning each defect also may be stored in memory 250 associated with the position data of each respective defect.

Figure 3:
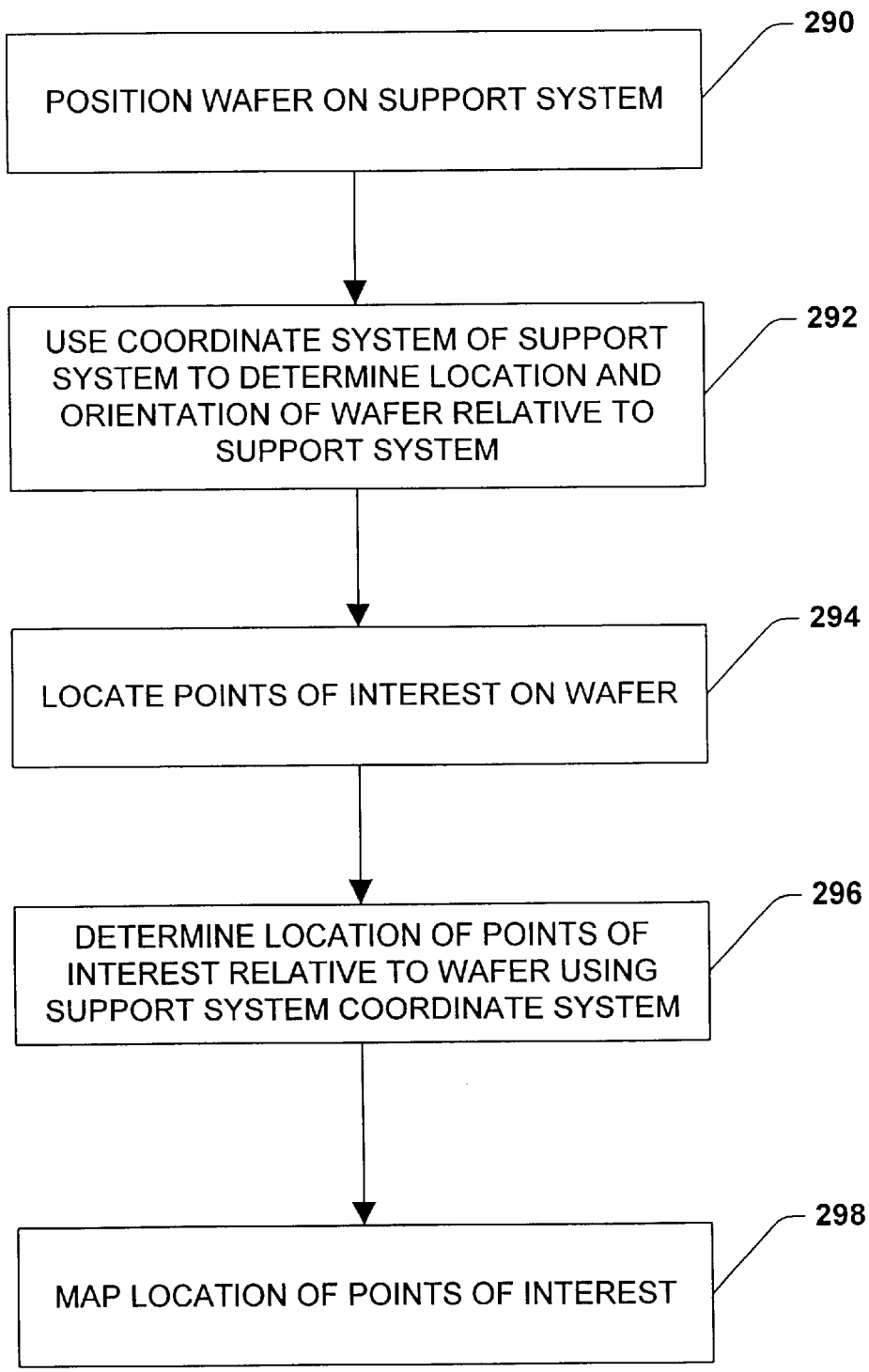
FIG. 3 is a flow diagram illustrating a process for locating defects of a wafer in accordance with the present invention.

FIG. 3 is a flow diagram which illustrates an exemplary methodology for locating points of interest on an object or article (e.g., a wafer) in accordance with the present invention. The method begins at step 290 in which the wafer is positioned on a support system, which includes a coordinate system. Next, the coordinate system of the support system is employed to determine the location and orientation of the wafer relative to the support system. From step 292, the method proceeds to step 294 in which one or more points of interest on the wafer are located. Such points of interest may include, for example, the wafer center and defects on the wafer surface, although other points of interest could be used. Next, at step 296, the location of each of the points of interest is determined relative to the wafer using the coordinate system of the support system. From step 296 the method proceeds to step 298 in which the relative location of each point of interest is mapped. Such mapping may include, for example, using a selected one of the points of interest as reference point relative to which the location of each other point of interest of the wafer is mapped.

The mapped locations may be stored in suitable memory. If the wafer is removed and then repositioned on the support system (step 290), the foregoing method may be employed to relocate each point of interest based on the stored mappings. The wafer does not have to be positioned on the support system at the same location and/or orientation as it was earlier placed. Instead, the location and orientation of the wafer relative to the support system are determined (step 292). The stored mappings are then employed to relocate the points of interest in the coordinate system of the support system relative to the location of the selected point of interest.

Figure 4:
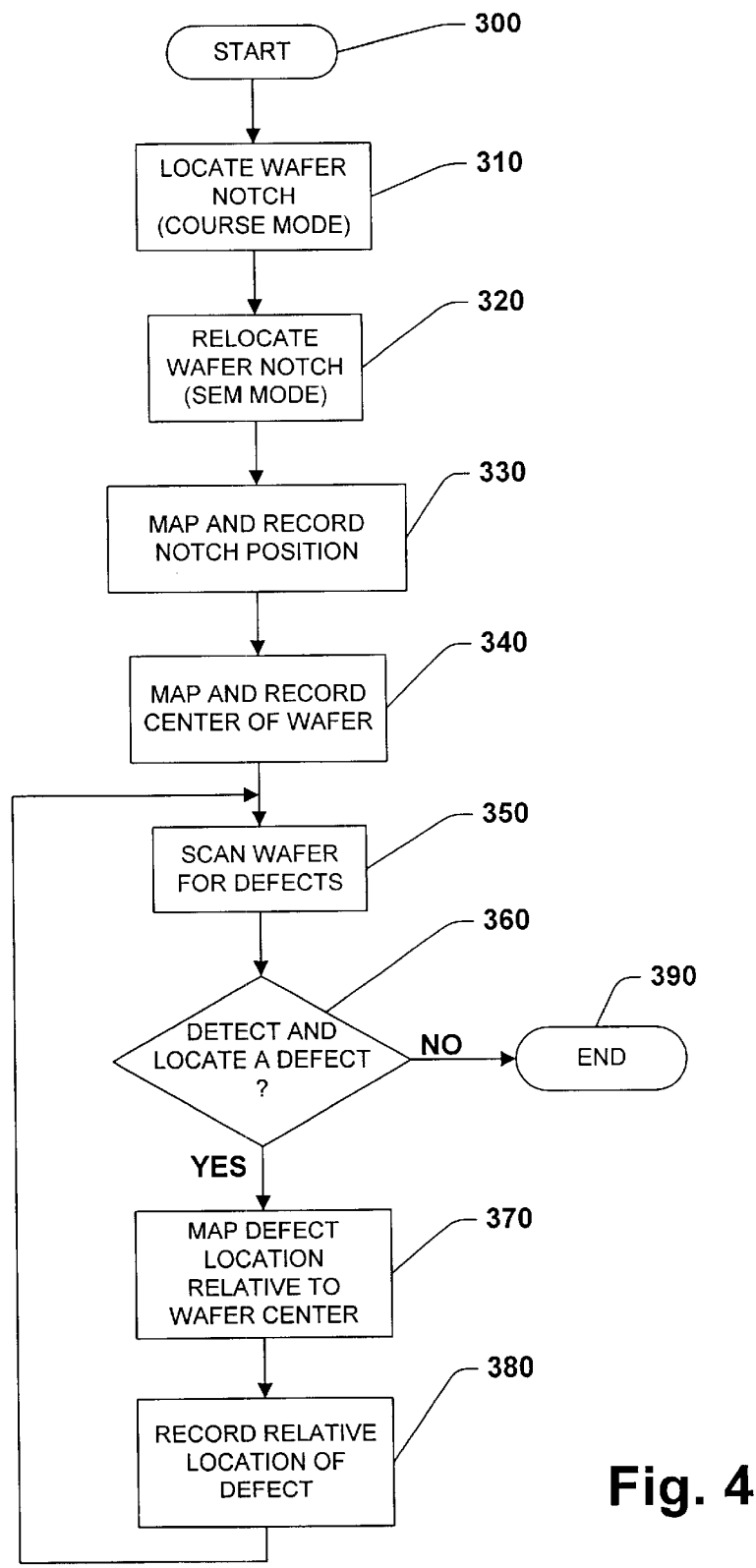
FIG. 4 is a flow diagram illustrating a process for locating defects of a wafer in accordance with the present invention

FIG. 4 is a flow diagram illustrating another exemplary method for locating defects on a wafer in accordance with the present invention. The method begins at step 300 in which the system 200 is initialized. This includes, for example, locating the reference markings 140 on the stage 120 of the scanning system 210 and mapping the markings to provide a corresponding reference coordinate system. Next, the wafer 110 is placed on the stage 120 of the associated scanning system 210. Once the wafer 110 is positioned on the stage, the process proceeds to step 310 in which the notch (or other orientation feature 130) is located. This is implemented, for example, by the SEM 210 operating in a course mode, wherein the SEM employs optical sensors to locate the notch. From step 310, the process proceeds to step 320 in which the wafer notch is relocated more precisely by the SEM operating in a SEM mode. The relocation of the notch begins with the SEM 210 using the optically located notch position as a reference position and then providing semi-fine adjustments of the notch position according to the resolution of the SEM.

After the notch has been located (step 320), the method proceeds to step 330 in which the position of the notch is mapped into the reference coordinate system and recorded. For example, distances between selected reference markings 140 of the stage 120 and the notch are determined and relative coordinates of the notch are determined based on the distance between the notch and reference markings. The determined relative coordinates of the notch position are recorded and the method proceeds to step 340. At step 340, the position of the center 150 of the wafer 110 is determined relative to the notch location and wafer center position is mapped into the reference coordinate system. The coordinates of the wafer center 150 in the reference coordinate system are recorded.

From step 340, the method proceeds to step 350 in which the SEM 210 scans the wafer 110 for defects. Next, at step 360, a determination is made as to whether a defect 160 has been located. If the determination at step 360 is positive, indicating that the defect 160 has been detected on the wafer 110, the method proceeds to step 370. At step 370, the location of the detected defect 160 is mapped relative to the wafer center 150. For example, the SEM 210 determines the location of the defect in the reference coordinate system of the stage 120 and provides corresponding X and Y coordinates for the defect. The processor 240 then determines the position of the detected defect relative to the wafer center 150. As described in the example of FIG. 1, this may be implemented by determining the relative position between the defect 160 and the wafer center 150 using polar coordinates with the wafer center used as center of the polar coordinate system.

The method proceeds to step 380 in which the determined location of the defect 160 relative to the wafer center 150 is recorded. From step 380, the process returns to step 350 to continue scanning the wafer 110 for defects. The method described above (steps 350–380) is repeated for the entire surface area of the wafer 110. After the entire surface of the wafer 110 has been scanned and the determination at step 360 is negative, the process proceeds to step 390 and the method ends.

It is to be appreciated that a number of other geometric reference points of the wafer 110 (other than wafer center 150) exist which could be implemented in accordance with the present invention. The position of any such reference point would be determined in the reference coordinate system of the stage 120 in substantially the same manner as described herein. A corresponding positional relationship between the reference point and each defect would then be determined and employed to calculated the relative location of the respective defect on the wafer 110. The use of any and all such relationships is intended to fall within the scope of the present invention as defined by the appended claims. The particular geometric relationship between the defects 160 and the selected reference point on the wafer 110 also will determine the appropriate coordinate transform needed to map between the various inspection tools and analyzing equipment being employed. Based on the above description, one skilled in the art could easily program the processor 240 of system 200 to determine the locations of defects 160 relative to the reference point in accordance with the examples of the present invention described herein.

Because the present invention determines the location of defects on the wafer 110 relative to a reference point of the wafer (independent of the inspection tool being employed), the location of such defects on the wafer may repeatedly be found as the wafer is loaded and reloaded into the SEM 210. Determining the location of the defects on the wafer 110 also is facilitated as the wafer is loaded and reloaded into other inspection tools by applying an appropriate coordinate transform to the recorded position data for the defects relative to the wafer reference point (center 150).

What has been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system for facilitating detection of defects on a wafer, comprising:
    a stage for receiving the wafer, the stage having a plurality of reference markings which form a reference coordinate system; and
    a scanning system associated with the stage for locating a defect of the wafer and mapping the defect relative to the reference coordinate system of the stage.

2. The apparatus of claim 1, wherein the wafer further includes an orientation indicating feature, the scanning system locating the feature in the reference coordinate system.

3. The apparatus of claim 2, wherein the feature is an alignment notch, the scanning system locating a center of the wafer relative to the position of the alignment notch in the reference coordinate system.

4. The apparatus of claim 3, further including a processor associated with the scanning system for determining the location of the defect relative to the wafer center.

5. The apparatus of claim 4, wherein the scanning system is a scanning electron microscope.

6. A system for facilitating detection of defects on a wafer, comprising:
    reference means for receiving the wafer and providing a stage having a reference coordinate system; and
    means for mapping a defect of the wafer relative to the reference coordinate system.

7. The apparatus of claim 6, wherein the means for mapping includes scanning means for scanning the wafer and locating a defect thereof.

8. The apparatus of claim 7, wherein the scanning means further includes means for locating an orientation feature of the wafer and locating a center of the wafer relative to the orientation feature in the reference coordinate system.

9. The apparatus of claim 8, wherein the means for mapping further includes processing means for mapping the location of the defect of the wafer relative to the center of the wafer and the orientation feature.

10. The apparatus of claim 7, wherein the reference means includes a stage having a plurality of reference markings that form the reference coordinate system.

11. The apparatus of claim 10, wherein the scanning system is a scanning electron microscope.

12. A method for facilitating detection of defects on a wafer located on a stage, the method comprising the steps of:
    locating reference markings on the stage; and
    mapping a defect of the wafer relative to reference markings of the stage.

13. The method of claim 12, further including the steps of locating an orientation feature of the wafer and mapping the location of the orientation feature relative to the reference markings.

14. The method of claim 13, further including the step of locating a center of the wafer relative to the mapped location of the orientation feature.

15. The method of claim 14, further including determining the location of the defect of the wafer relative to the center of the wafer.

16. The method of claim 15 further including mapping the determined location of the defect of the wafer relative to the center of the wafer and the orientation feature.

17. The method of claim 13, wherein the reference markings form a reference coordinate system, the method further including the step of locating a center of the wafer relative to the orientation feature in the reference coordinate system.

18. A system for mapping a wafer, comprising:
    a support system for supporting the wafer, the support system having a stage reference coordinate system associated therewith;
    a locating system for determining via the reference system a position and orientation of the wafer relative to the support system;
    a mapping system for mapping the position and orientation of the wafer based on information from the locating system, the mapping system further mapping at least one point of interest on the wafer surface; and
    a system for storing the mapping information.

19. A system for mapping a wafer, comprising:
    a stage for supporting the wafer, the stage including a plurality of reference marks;
    a system for determining location and orientation of the wafer relative to the stage via the reference marks;
    a system for detecting points of interest on the wafer;
    a system for determining the location of the points of interest relative to the wafer via the reference marks; and
    a system for mapping the location of the points of interest relative to the wafer.

20. A wafer stage, comprising:
    a top surface for supporting a wafer, the top surface including a stage having a plurality of reference marks which facilitate determining a location and orientation of the wafer relative to the stage, and further facilitate determining location of at least one point of interest on the wafer relative to the wafer and stage.

* * * * *